United States Patent [19]

Piesch

[11] 4,163,835

[45] Aug. 7, 1979

[54] PREPARATION OF ELECTROLYTE-FREE AMINOPLAST RESINS

[75] Inventor: Steffen Piesch, Oberursel, Fed. Rep. of Germany

[73] Assignee: Cassella Aktiengesellschaft, Frankfurt, Fed. Rep. of Germany

[21] Appl. No.: 760,651

[22] Filed: Jan. 19, 1977

[30] Foreign Application Priority Data

Jan. 31, 1976 [DE] Fed. Rep. of Germany ....... 2603768

[51] Int. Cl.$^2$ .................... C08G 12/30; C08G 12/32
[52] U.S. Cl. .................... 528/254; 528/261; 544/196
[58] Field of Search .................. 260/67.6 R; 544/196; 528/254, 231, 261

[56] References Cited

U.S. PATENT DOCUMENTS 3,965,058   6/1976   Yurcheshen et al. ........... 260/67.6 R

FOREIGN PATENT DOCUMENTS 158677   9/1954   Australia ................................. 544/196
474160   6/1951   Canada ................................... 544/196

*Primary Examiner*—Allan Lieberman
*Attorney, Agent, or Firm*—Connolly and Hutz

[57] ABSTRACT

Electrolyte-free etherified methylolaminotriazines are directly prepared by reacting together in the absence of electrolyte, the aminotriazine, formaldehyde and certain ether-alcohols. When the formaldehyde to aminotriazine mol ratio is sufficiently high and the etherification sufficiently extensive, the resulting products are particularly desirable in that they are quite stable and thermoset to exceptionally elastic, cured products having high electrical, moisture, and temperature resistance.

12 Claims, No Drawings

PREPARATION OF ELECTROLYTE-FREE AMINOPLAST RESINS

The present invention relates to thermosetting etherified methylolaminotriazine condensation products.

Among the objects of the present invention is the provision of such products which are electrolyte-free, improved methods for preparing them as well as thermoset products produced from them.

The foregoing as well as additional objects of the present invention will be more fully understood and appreciated from the following description of several of its exemplifications.

According to the present invention very desirable thermosetting electrolyte-free etherified methylolaminotriazine condensation products are prepared by condensing the aminotriazine, in the absence of electrolyte, with from about 1.3 mols to 2 n mols of formaldehyde pr mol of aminotriazine where n is the number of amino groups in the aminotriazine, in excess of etherifying alcohol having the formula

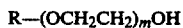

$$R—(OCH_2CH_2)_mOH$$

R denoting an alkyl group with 1 to 4 C atoms and m representing an integer from 1 to 4, by heating such a condensation mixture to from about 50° to about 180° C. until the condensation has taken place and the degree of etherification is at least about 33%.

Preferred condensation products of the present invention have at least about 50% etherification, or are condensed in the proportion of at least about 1.8 mols of formaldehyde, especially of from about 1.8 mols to 1.2 n mols formaldehyde per mol of diaminotriazine or triaminotriazine, or are etherified with alcohols in which R is methyl or m is 1 or 2, or the aminotriazine is melamine, or have any combination of these preferred aspects.

The etherified condensation products of the present invention are very readily manufactured inasmuch as only a one-step reaction is needed and a zero content of electrolyte can be assured without the complication of having to remove the catalytic materials such as acids that are used in the prior art to produce similar products. The condensation products of the present invention also produce better thermoset products of improved elasticity, particularly for use where high electrical resistance and/or high electrical surface resistivities (tracking resistance) and/or high moisture resistance, and/or resistance to heat and temperature changes are desired. The etherified uncured condensates of the present invention also have particularly long pot life.

Examples of etherifying alcohols, which can be used for the manufacture of the etherified methylolaminotriazines are glycol monomethyl ether, glycol monoethyl ether, diglycol monomethyl ether, diglycol monoethyl ether, diglycol monopropyl ether, triglycol monomethyl ether, triglycol monoethyl ether, triglycol monopropyl ether, triglycol monobutyl ether, tetraglycol monomethyl ether, tetraglycol monoethyl ether, tetraglycol monopropyl ether and tetraglycol monobutyl ether. Examples of aminotriazines which can be used are melamine, formoguanamine, benzoguanimine and acetoguanamine.

It was surprisingly found that the co-presence of the aminotriazine, the formaldehyde, and any of the above-noted ether-alcohols, causes the etherification to take place along with the condensation, without the need for the electrolytes heretofore used for etherification, and that the molar ratio of aminotriazine to formaldehyde can be varied within considerably wider limits than has hitherto been known in the case of normal etherified melamine-formaldehyde condensation products. It is helpful to have an excess of the ether-alcohol in the reaction mixture since it speeds the reaction, and at least about 20% excess is desirable. The presence in the reaction mixture of more than about 20 mols of ether-alcohol per mol of aminotriazine is not helpful and unnecessarily dilutes the condensation product.

For best results the reaction mixture should be anhydrous. The presence of water slows down the reaction, but up to about 10% water by weight does not slow it down too much and mixtures containing up to that much water can be considered essentially anhydrous.

Some water forms during the etherification portion of the reaction, and if this brings the total water content above about 10%, it is helpful to boil off the excess water during the course of the reaction. When the reaction is conducted at temperatures that do not cause the water to boil off at atmospheric pressure, the reaction can be conducted at lower pressures.

It is very helpful to follow the course of the reaction by measuring the quantity of water formed. Thus by starting with an anhydrous reaction mixture and using temperatures and pressures that cause water to boil off, the vapors given off by the reaction mixture can be fractionally condensed to separately condense out the boiled-off water into a measuring container. An inspection of the amount of water thus collected will then show how much etherification has taken place. Such measurement can also be made when the initial reaction mixture contains some water, a corresponding correction being made to the measured values, but the accuracy of such determination is then poorer.

After the desired degree of etherification has been achieved, the excess ether-alcohol remaining in the reaction mixture can be partially or completely removed by distillation, preferably in vacuo. It is not necessary to wait until the etherification has reached the desired degree before commencing the removal of excess ether-alcohol. Such removal can be initiated at the start of the reaction or as soon thereafter as there is no danger of boiling away too much formaldehyde. Volatiles can be removed to leave a residue containing at least 25% by weight of the etherified condensation product.

The formaldehyde is preferably employed in the form of paraformaldehyde. It is, howver, also possible to use aqueous solutions of formaldehyde or solutions of formaldehyde in the ether-alcohol. If aqueous formaldehyde solutions are employed, the water thereby brought in is at first distilled off from the reaction mixture at normal pressure. Even when this procedure is applied, only very little formaldehyde is concurrently distilled off. The loss of formaldehyde is not more than 1 to 2%.

Preferred reaction temperatures are between about 80° and about 140° C. This range provides a good reaction velocity and reduces the risk that the reaction product will become over-condensed and insoluble.

As the condensation-etherification reaction is carried out in the absence of an acid, self-etherification of the etherifying alcohol is impossible to occur.

As in the case with other condensation reactions between aminotriazines and formaldehyde, the product obtained through the condensation-etherification reaction of the present invention is chemically not a substance with a uniform structure but a mixture of different substances. Therefore, the numerical data relating to the structure of the product are statistical ones.

Owing to the absence of acid catalysts, neutralization of the reaction mixtures is not necessary, so that completely electrolyte-free products may be obtained.

The freedom from electrolyte is a decisive factor in the outstanding electrical properties of the mouldings according to the invention and the wide range of degree of methylolation permits the properties of the products according to the invention to be adjusted even to extreme industrial demands, with special reference to elasticity, resistance to water and resistance to heat and changes of temperatures.

The crude product of the condensation-etherification reaction is soluble in water and other solvents, and can be used to prepare molded bodies, laminates, coatings, and the like in manners similar to those in which prior art etherified condensates of this type are used. Such techniques are described for instance in German Auslegeschrift No. 24 19 124, German Auslegeschrift No. 24 30 899, and in standard texts.

The manufacture of moldings with the condensation-etherification products of the invention is carried out for example by combining such a product with a carrier sheet or web, or with a filler, and pressing the resulting compositions under pressure at elevated temperature. Alternatively, the condensation-etherification product can be impregnated, for example, into absorbent sheet-like materials such as textile webs composed of natural or synthetic fibers, especially cellulose fibers, or into randam fiber fleeces, in particular absorbent paper, or into wood veneers. The impregnation can be carried out in a known manner, for example by application with brushes or rollers, spraying-on or dipping, the general procedure being such that the impregnated materials contain 25 to 75%, preferably 25 to 50%, and most preferably 30 to 40% of the aminoplast resin. After impregnation, the materials are dried to a residual moisture content of 1 to 11%. The sheet-like combinations thus obtained are laid one on top of another in several layers and are pressed to form moldings, conveniently at temperatures between 110° and 170° C. and pressures between 2.0 and 800 kp/cm$^2$*.

*1 kp/cm$^2$=14.22 lbs./inch$^2$

Other additives such as pigments, plasticizers, flow auxiliaries and slip or release agents, can also be included in the molding mixtures. Known fillers which may be used with aminoplast resins of the present invention are, for example, wood flour, cellulose powder including cellulose ester powder, cotton flock, flour, starch, peat, waste wood particles, ground materials, asbestos fibers or graphite, of which the first two mentioned are preferred. Pigments which may be used as the compositions of the present invention can be organic or inorganic. Suitable inorganic pigments are generally sulphides, oxides or mixed oxides of metals, especially of titanium, zinc, iron, chromium, cobalt, lead and cadmium. Carbon black is a preferred black pigment. Possible organic pigments are the compounds characterized in the Colour Index as pigment dyes.

Known flow auxiliaries which may be used include sorbitol, glycols and glycol derivatives and polyglycols.

Metal stearates, preferably zinc stearate and magnesium stearate, may additionally be employed as slip agents or release agents, for trouble-free release of the molding from the compression mold.

The aminoplast resins are mixed with the filler and optionally the further additives in known manner, for example, in kneaders or drum mixers and this process can be carried out at elevated temperatures from 70° to 140° C., preferably from 105° to 120° C. In relation to the energy required for kneading and the homogeneity of the combination which can be achieved, kneading at elevated temperature gives substantial advantages. After mixing, the resulting combination is cooled to room temperature and generally solidifies. The solid product may be granulated and can then be pressed.

Pressing is generally carried out at temperatures between 120° and 180° C., preferably 140° and 170° C., under pressures of 200 to 800 kp/cm$^2$, preferably 400 to 600 kp/cm$^2$. The pressing time is usually from 10 to 60 minutes for the manufacture of molded laminates and 30 seconds to 5 minutes for the manufacture of moldings using pulverulent fillers (further described hereinbelow). Compression molding compositions obtained by using pulverulent fillers can contain 40 to 70%, preferably 50 to 60%, of the aminoplast resin.

Surface coatings using the compositions of the present invention are generally manufactured in such a way that, as in the manufacture of molded laminates, a sheet-like carrier material is first impregnated with the aminoplast resin of the present invention as described above and the resin content of the composition can be from 25 to 45, preferably from 30 to 40%, relative to the weight of the total combination. As also described above, the impregnated carrier materials are subsequently dried to a residual moisture of from 3 to 10%. The sheet-like resin-carrier combinations thus obtained are pressed onto the surfaces to be coated under a pressure of from 2 to 12 kp/cm$^2$, preferably from 4 to 6 kp/cm$^2$, and at temperatures from 110° to 170°, preferably from 140° to 150° C. The pressing time is generally from 30 seconds to 4 minutes, preferably from 1 to 2 minutes.

If desired, decorative surface coatings may be manufactured in this way by using a suitable printed or dyed decorative paper as the sheet-like resin carrier material. Curved surfaces, such as, for example, profiled moldings, can also be coated in a trouble-free manner in accordance with the invention, owing to the extremely high elasticity of the cured thermoset products thus made. It is also possible by reason of such high elasticity to coat chipboards all round, by wrapping a fully or partially cured sheet molded according to the present invention, around the edges of a board and then hot pressing such assembly. In the prior art it was necessary to separately coat the individual plane surfaces of such a board.

If desired, it is also possible, in the case of the sheet-like compositions used to manufacture moldings, to print the web-like carrier materials in a decorative manner with organic pigments before the impregnation or, if sheet-like carrier materials containing cellulose fibers or textile fibers are involved, to dye or to print the carriers with textile dyestuffs.

In order to manufacture laminates from the sheet-like compositions, several layers are pressed together at temperatures from 110° to 170° C., preferably 130° to 150° C., and at a pressure of from 2.0 to 800 kp/cm$^2$, preferably 50 to 120 kp/cm$^2$, and most preferably 80 to 100 kp/cm$^2$.

The molded laminates manufactured using the aminoplast resins according to the present invention are distinguished by an outstanding elasticity and, at the same time, very good resistance to water. Owing to their extremely high resistance values and their high tracking resistance, they are outstandingly suitable for the manufacture of components in the electrical industry, such as printed circuits, core formers for coils and transformers, parts in switches and relays, tube sockets and the like. The same valuable properties are also displayed by moldings which have been manufactured using the aminoplast resins according to the invention in combination with pulverulent fillers. Further advantages of the moldings and surface coatings which can be manufactured in accordance with the invention are their resistance to high and low temperatures and to changes in temperature, and their excellent Martens heat distortion point, high impact strength, high flexural strength, and low after-shrinkage.

EXAMPLE 1

5,300 ml. of glycolmonomethylether, 1,372 g. of melamine and 650 g. of p-formaldehyde are stirred at 120° C. A clear solution forms after 1½ hours. Approximately 1.5 liters of the ether-alcohol containing some water are then distilled off at atmospheric pressure. This gives a melamine resin solution which contains 66% of condensation product (determined by the loss of weight of a sample when heated at 120° C. for 1 hour), which can be diluted with water to an unlimited extent and which can be diluted with 1 part of n-butanol for each part of resin solution by volume, without becoming turbid at 20° C. The analysis of the product before dilution shows it to have, by weight, 15.4% bound formaldehyde and 21.3% bound glycolmonomethylether.

EXAMPLE 2

1,260 g. of melamine, 450 g. of p-formaldehyde and 6 liters of glycolmonomethylether are stirred for 1½ hours at a bath temperature of 140° C. A solution is formed. 1.5 liters of the ether-alcohol are not distilled off. The residual crude resin solution can be diluted with water in a ratio of 1:2.0 (that is to say 1 ml. of resin takes up 2 ml. of water at 20° C. without becoming turbid) and can be diluted with n-butanol in a ratio of 1:0.8, and can be diluted with glycolmonomethylether to an unlimited extent. The crude resin solution contains 53% of condensation product (1 hour at 55° C./20 mm Hg) and the viscosity, measured in a Ford beaker according to DIN* 53,211 with a 4 mm. nozzle, is 18.5 seconds.
*DIN=Deutsche Industrie Normen (German Industrial Standards)

EXAMPLE 3

126 g. of melamine, 40 g. of p-formaldehyde and 500 ml. of glycolmonomethylether are stirred for 2 hours at a bath temperature of 140° C.; a clear solution is formed. About 200 ml. of the glycolmonomethylether are now distilled off. A 62% strength resin solution (the strength is determined as above), which contains 11.2% of formaldehye and 18% of glycolmonomethylether in a bound form, is obtained.

EXAMPLE 4

126 g. of melamine, 90 g. of p-formaldehyde and 1.2 liters of glycolmonobutylether are stirred at 140° C. in an apparatus with a descending condenser until no further water drops from the condenser. 500 ml. of the glycolmonobutylether are distilled off in vacuo, leaving a 60% strength resin which can be diluted with n-butanol to an unlimited extent.

EXAMPLE 5

187 g. of benzoguanamine, 120 g. of p-formaldehyde and 1 liter of glycolmonomethylether are heated to 120° C. for 20 minutes; a clear solution is formed. 600 ml. of the glycolmonomethylether and water are now distilled off. 540 g. of a 62% strength resin which has unlimited miscibility with n-butanol, can be distilled with 4 parts of xylene and can be diluted with water in a ratio of 1:2, is obtained. Its viscosity is 17 seconds (4 mm. Ford beaker) according to DIN 53,211.

EXAMPLE 6

126 g. of melamine, 180 g. of p-formaldehyde and 1.2 liters of glycolmonomethylether are boiled under reflux for 1 hour, and 800 g. of the glycolmonomethylether and water are then distilled off slowly. There are thus obtained 730 g. of an 80% strength resin which can be diluted with water or n-butanol to an unlimited extent.

EXAMPLE 7

1,008 g. of melamine, 800 g. of p-formaldehyde and 8 liters of glycolmonomethylether are boiled under reflux for 8 hours and approximately 6 liters of the glycolmonomethylether and water are then distilled off. This leaves 3 kg. of a 91% strength resin which is miscible with water in all proportions.

EXAMPLE 8

7 liters of diglycolmonomethylether, 630 g. of melamine and 480 g. of p-formaldehyde are heated to 120°-130° C. under a subatmospheric pressure of 400-500 mm. Hg, while stirring. In the course thereof, 600 ml. water of reaction are removed by distillation. The excess diglycolmonomethylether (approximately 4 liters) is now distilled off at 100° C. bath temperature under a vacuum of 10 mm. Hg. This recovered diglycolmonomethylether can be used again in further reaction batches. There remains 2.1 kg. of 70% strength resin (the strength is determined by distilling over all of its free ether at atmospheric pressure and weighing the amount thus distilled over), which is miscible with water in all proportions. This resin solution can be diluted in the following ratios with the following solvents:
Toluene 1:10
n-Butanol 1:3
Methanol 1:00

If triglycolmonomethylether or triglycolmonoethylether is used in place of the methyldiglycol and the procedure is otherwise as described in Example 8, similar results are obtained. With these very high-boiling glycol derivatives it is advisable to carry out the concentrating operation under 1 mm. Hg using a thin film evaporator.

The examples which follow illustrate some of the possibiliies for use of the aminoplast resins according to the present invention.

EXAMPLE 9

10 sheets of an electrolyte-free paper weighing 80 g/m² are impregnated in the aminoplast resin solution of Example 1. After drying, which is carried out at 130° C., the resin content is about 60% and the residual moisture content (determined by drying a sample at 160° C. for 5 minutes) is about 6%. The thus-impregnated papers are laid one on top of another and are pressed in a multi-roll press between nickel sheets chromium-plated to a high gloss, for a period of 15 minutes at a temperature of 140° C. and under a pressure of 80 kp/cm².

After cooling the laminate under pressure to approximately 70° C. a laminate 1.1 mm. thick is obtained. Testing this laminate gives the following data:
Curing stage in Kiton test: 2–3
Electrical surface resistance DIN 53,482: $5.5 \times 10^{12}$ ohms
Tracking resistance DIN 53,480: stage KA 3b.

The Kiton test is performed by immersing half of the material on test in a boiling solution of the following composition:
1 l. water
5 ml. conc. sulfuric acid
1 ml. of 2% aqueous solution of Kitonechtrot 2 BL (see C.I. Acid Red 45) for 10 minutes.

Thereafter the grade of coloring is compared with that shown on a six-graded scale according to which
grade 1 indicates no coloring
grade 6 indicates considerable coloring
Grade 1 is attributable to an overcured surface and grade 6 to an uncured surface. A perfect cured surface has a Kiton-test grade of 2.

EXAMPLE 10

A paper printed with brown dye in a wood-grain pattern and weighing 80 g./m² is impregnated in a solution, diluted with water to 40% by weight of solid resin, of the aminoplast resin of Example 7. The resin content of the impregnated paper is approximately 38% and it is then dried to a residual moisture content approximately 2%.

This resin-bearing paper is glued cold onto a chipboard, using a polyvinyl acetate cement. Lengths of the paper corresponding to the thickness of the board are arranged to project beyond the edges of the chipboard and the latter are encased by bending the projecting paper lengths around the edges and cementing then there with the polyvinyl acetate cement. The paper is so elastic that no cracks are formed during the encasing. The encased chipboard sheet can then be provided with a coating of an acid-curing lacquer.

EXAMPLE 11

70 parts of the crude resin solution of Example 6, 30 parts of microcellulose, 4 parts of titaniumdioxide and 1 part of zinc stearate are mixed and rolled out into a milled sheet on a roll mill at 110° C. The sheet is then granulated and the granules molded in a standard bar mold at 150°–155° C. and 250 kp/cm² with a compression time of 10 minutes to yield a body that has the following properties:
Flexural strength according to DIN 52,362: 840 kp/cm²
Tracking resistance according to DIN 53,480: KA3c
Martens heat distortion point (DIN 53,462): 121° C.
After-shrinkage according to DIN 53,464: 1%
Impact strength according to DIN 53,453: 7 kpcm/cm².

EXAMPLE 12

The method of Example 8 was repeated to prepare 2.1 kg. of 70% strength resin miscible with water in all proportions. It could be diluted in the following ratios with the following solvents:
Toluene 1:10
n-Butanol 1:3
Methanol 1:∞

The 70% strength resin was diluted with isopropyl alcohol to a resin concentration of approximately 45%. 2% of p-toluenesulphonic acid (relative to solid resin) was added in order to accelerate curing. A cellulose carrier web weighing approximately 250 g./m² is impregnated in the thus-distilled solution to a resin content of approximately 25% relative to the final weight of the impregnated paper, and the impregnated web is dried at 130° C. to a residual moisture content of 1%. The curing of the resin in the sheet takes place at the same time as the drying. The cured sheet is then given a lacquer coating, approximately 30 g./m², of an acid-curing commercially available lacquer, and is glued as a highly elastic overlapping edge band around the edges of a chipboard using a hot-melt ethylenevinyl acetate copolymer adhesive.

EXAMPLE 13

The method of Example 8 was again repeated to provide approximately 2.1 kg. of a 70% strength resin miscible with water in all proportions. The resin solution is then diluted with water to 50% resin strength, and pieces of wood veneer 0.8 mm. thick are impregnated in it to a resin content of approximately 28–32%, and are then dried in a circulating air oven to a residual moisture content of 7–8%. 10 layers of this wood veneer are pressed between nickel sheets chromiumplated to a high gloss, at 140° C. under a pressure of 110 kp/cm² and for a period of 18 minutes, to produce a very desirable board sheet having the following properties:
Flexural strength according to DIN 52,362: 2,237 kp/cm²
Impact strength according to DIN 53,453: 21.2 kpcm/cm²
Water pick-up after 96 hours at 60° C. 11.7%.

No cracks are formed on subjecting the sheet to an alternating heat treatment of 3 cycles in each of which the sheet is first heated for 20 hours at 80° C., and then cooling to 20° C.

Similar results are obtained with other aminotriazines such as benzoguanamine and acetoguanamine.

EXAMPLE 14

2.5 l. of triglycol monomethyl ether, 126 g. of melamine and 470 g. of aqueous formaldehyde solution of 39% strength are heated to 50°–60° C. under a vacuum of 400–500 mm. Hg, whilst stirring until about 200 ml. of water are removed by distillation. Then heating and stirring is continued without vacuum at a temperature of between 140° and 150° C. until no further water distills over. The excess triglycol monomethyl ether is now distilled off under a vacuum of 100–150 mm. Hg. This recovered triglycol monomethyl ether can be used again in further batches.

The so obtained resin is miscible with water, isobutanol and toluene in all proportions.

EXAMPLE 15

2,000 ml. of monomethyl ether glycol, 3,000 ml. of triglycolmonomethyl ether, 1,372 g. of melamine and 650 g. of p-formaldehyde are stirred at 120° C. A clear solution is formed after 1½ hours. Then approximately 1.5 liters of the glycols are distilled off. This gives a melamine resin solution which can be diluted with water to an unlimited extent.

The crude products of Examples 1 through 8, 14 and 15 can be stored for 26 weeks without significant loss of effectiveness, particularly if the storage is at 10° C. or below, or if the excess ether-alcohol is not removed or is not entirely removed. The presence of up to about 50% by weight free ether-alcohol in the uncured resin when it is subjected to the curing process, does not detract from the properties of the cured product.

Useful products pursuant to the present invention are also formed when two or more of the above-noted ether-alcohols are present in the reaction mixture, and/or two or more amino-triazines are present.

Obviously many modifications and variations of the present invention are possible in the light of the above teachings. It is, therefore, to be understood that within the scope of the appended claims the invention may be practiced otherwise than as specifically described.

What is claimed:

1. A process for the manufacture of an electrolyte-free etherified methylolaminotriazine, wherein in the absence of electrolyte the aminotriazine is condensed with from about 1.3 mols to 2 n mols of formaldehyde per mol of aminotriazine where n is the number of amino groups in the aminotriazine, in an excess of etherifiying alcohol having the formula $$R-(OCH_2CH_2)_mOH$$

R denoting an alkyl group with 1 to 4 C atoms and m representing an integer from 1 to 4, by heating such a condensation mixture having a water content of not over about 10% by weight to from about 50° to about 180° C. until the condensation has taken place and the degree of etherification is at least about 33%.

2. The process of claim 1 in which the condensation mixture contains up to about 20 mols etherifying alcohol per mol of the aminotriazine.

3. The process of claim 2, wherein at least about 1.8 mols of formaldehyde are condensed per mol of the aminotriazine.

4. The process of claim 2, wherein the heating is continued until the degree of etherification is at least about 50%.

5. The process of claim 2, wherein the aminotriazine is a diaminotriazine or a triaminotriazine, and from about 1.8 mols to 1.2 n mols of formaldehyde are condensed per mol of the diaminotriazine or triaminotriazine.

6. The process of claim 1 wherein R is methyl.

7. The process of claim 1 wherein m is 1 or 2.

8. The process of claim 1 wherein the aminotraazine is melamine.

9. The process of claim 1 wherein the heating is effected at from about 80° to about 140° C.

10. The process of claim 1 in which the heating is followed by boiling off volatiles to leave a residue containing at least 25% by weight of the etherified condensation product.

11. The process of claim 1 in which the heating is conducted in a manner that causes water in the mixture to be boiled away.

12. The process of claim 11 in which the condensation mixture is anhydrous when the heating is started, and the quantity of water boiled away during the heating is measured to determine the degree of etherification.

* * * * *